(12) United States Patent
Reves et al.

(10) Patent No.: US 11,690,974 B2
(45) Date of Patent: Jul. 4, 2023

(54) METHODS AND DEVICES FOR DELIVERING THERAPEUTIC MATERIALS TO THE INTERVERTEBRAL DISC

(71) Applicant: Warsaw Orthopedic, Inc., Warsaw, IN (US)

(72) Inventors: Benjamin T. Reves, Memphis, TN (US); Todd M. Boyce, Collierville, TN (US); Daniel A. Shimko, Germantown, TN (US); Jared T. Wilsey, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 317 days.

(21) Appl. No.: 16/394,854

(22) Filed: Apr. 25, 2019

(65) Prior Publication Data

US 2020/0338307 A1 Oct. 29, 2020

(51) Int. Cl.
| | |
|---|---|
| *A61M 25/00* | (2006.01) |
| *A61M 25/06* | (2006.01) |
| *A61M 29/00* | (2006.01) |
| *A61M 5/32* | (2006.01) |
| *A61K 9/06* | (2006.01) |
| *A61B 17/16* | (2006.01) |
| *A61M 25/09* | (2006.01) |

(52) U.S. Cl.
CPC ..... *A61M 25/0084* (2013.01); *A61B 17/1671* (2013.01); *A61K 9/06* (2013.01); *A61M 5/32* (2013.01); *A61M 25/065* (2013.01); *A61M 29/00* (2013.01); *A61M 2025/0091* (2013.01); *A61M 2025/09183* (2013.01); *A61M 2202/0415* (2013.01); *A61M 2202/0427* (2013.01); *A61M 2202/0468* (2013.01); *A61M 2202/09* (2013.01); *A61M 2202/10* (2013.01); *A61M 2205/0266* (2013.01); *A61M 2210/1003* (2013.01)

(58) Field of Classification Search
CPC ........... A61B 17/1671; A61B 17/3472; A61M 2210/1003; A61M 25/0084; A61M 25/0085; A61M 2025/0089; A61M 2025/0092; A61M 2025/0095; A61K 9/0085
See application file for complete search history.

(56) References Cited

U.S. PATENT DOCUMENTS

| | | |
|---|---|---|
| 5,172,702 A | 12/1992 | Leigh et al. |
| 5,284,479 A | 2/1994 | de Jong |
| 6,517,568 B1 | 2/2003 | Sharkey et al. |

(Continued)

OTHER PUBLICATIONS

International Search Report for PCT/US2020/028950 dated Jul. 29, 2020.

(Continued)

*Primary Examiner* — Theodore J Stigell
*Assistant Examiner* — Rachel T. Smith
(74) *Attorney, Agent, or Firm* — Fox Rothschild LLP

(57) ABSTRACT

A method of delivering a therapeutic agent to a nucleus pulposus of an intervertebral disc is provided. The method comprises inserting a delivery tool containing the therapeutic agent through an anterior portion, a lateral portion, or an anterolateral portion of an annulus fibrosus and into the nucleus pulposus of the intervertebral disc; and delivering the therapeutic agent to the nucleus pulposus of the intervertebral disc. Devices and kits are also provided.

4 Claims, 11 Drawing Sheets

(56) References Cited

U.S. PATENT DOCUMENTS

| | | | |
|---|---|---|---|
| 7,824,390 B2 | 11/2010 | Miller et al. | |
| 7,963,970 B2 | 6/2011 | Marino | |
| 8,052,661 B2 | 11/2011 | McGuckin, Jr. et al. | |
| 8,082,043 B2 | 12/2011 | Sharkey et al. | |
| 8,444,694 B2 | 5/2013 | Collins et al. | |
| 8,540,684 B2 | 9/2013 | Yeung et al. | |
| 8,790,375 B2 | 7/2014 | Ali | |
| 8,926,552 B2 | 1/2015 | Walsh | |
| 9,113,950 B2 | 8/2015 | Schultz et al. | |
| 2001/0007933 A1* | 7/2001 | Lesh | A61M 25/0133 604/272 |
| 2003/0130621 A1 | 7/2003 | Bryan et al. | |
| 2005/0187556 A1 | 8/2005 | Stack et al. | |
| 2006/0122704 A1 | 6/2006 | Vresilovic et al. | |
| 2006/0206116 A1 | 9/2006 | Yeung | |
| 2007/0168041 A1 | 7/2007 | Kadiyala | |
| 2007/0243228 A1* | 10/2007 | McKay | A61P 29/00 424/426 |
| 2007/0255285 A1 | 11/2007 | Trieu | |
| 2007/0293813 A1 | 12/2007 | Spenciner | |
| 2008/0208196 A1 | 8/2008 | Daum | |
| 2009/0018507 A1 | 1/2009 | Schmitz et al. | |
| 2009/0099660 A1 | 4/2009 | Seifert et al. | |
| 2011/0009873 A1 | 1/2011 | Schraga | |
| 2013/0012951 A1* | 1/2013 | Linderman | A61B 17/1642 606/93 |
| 2013/0060233 A1* | 3/2013 | O'Connor | A61M 5/14248 604/506 |
| 2014/0046245 A1 | 2/2014 | Cornacchia | |
| 2015/0230789 A1 | 8/2015 | Wales et al. | |
| 2016/0051306 A1* | 2/2016 | Sasaki | A61B 17/1659 606/93 |
| 2016/0074217 A1 | 3/2016 | Price et al. | |
| 2016/0367267 A1* | 12/2016 | Marino | A61B 17/1671 |
| 2017/0055968 A1* | 3/2017 | O'Callaghan, Jr. | A61M 25/0102 |
| 2018/0099009 A1* | 4/2018 | Binette | A61M 1/815 |
| 2018/0256364 A1 | 9/2018 | Sandhu | |
| 2019/0008528 A1 | 1/2019 | Lopez | |
| 2019/0029844 A1 | 1/2019 | Schaller et al. | |

OTHER PUBLICATIONS

2009 ISSLS Prize Winner: Does Discograpy Cause Accelerated Progression of Degeneration oChanges in teh Lumbar Disc—A Ten-Year Matched Cohort Study, Eugene J. Carragee, MD, et al., Spine, vol. 34, No. 21, pp. 2338-2345 © 2009, Lippincott Williams & Wilkins.

Mechanism of Diapedesis: Importance of the Transcellular Route, Marie-Dominique Filippi, HHS Public Access, Author Manuscript, Adv Immunol. 2016; 25-53:10.1016/bs.ai.2015.09.001.

A Simple Disc Degeneration Model Induced by Percutaneous Needle Puncture in the Rat Tail, Bin Han, MD, et al., Spine, vol. 33, No. 18, pp. 1925-1934, © 2008, Lippincott Williams & Wilkins.

European Search Report in Application No. 20794609.6 dated May 2, 2023.

* cited by examiner

METHODS AND DEVICES FOR DELIVERING THERAPEUTIC MATERIALS TO THE INTERVERTEBRAL DISC

BACKGROUND

The human spine is formed from twenty-six consecutive vertebrae. Each of these vertebrae is separated from any adjacent vertebra by an intervertebral disc that functions to absorb shock and prevent each vertebra from directly impacting upon another vertebra. At the center of each disc is a gel-like inner layer made from proteoglycan called the nucleus pulposus and around the nucleus pulposus is a relatively tough outer ring layer called the annulus fibrosus. Degenerative disc disease refers to any of the common degenerative conditions of the lower spine involving degeneration of the disc.

As humans age, their spine will begin to show signs of degeneration. Generally, degeneration is associated with the loss of proteoglycan from the nucleus pulposus and a reduction of the disc's ability to absorb shock between vertebrae. Although some affected patients may not exhibit symptoms, many affected patients suffer from chronic back and/or leg pain. Pain associated with disc degeneration may become debilitating and may greatly reduce a patient's quality of life.

In recent years, a number of regenerative therapies have been developed to treat degenerative discs. The regenerative therapies often use therapeutic materials that are delivered to the nucleus pulposus of the disc to treat pain and/or degeneration. However, these therapies require medical procedures which require penetration of the annulus fibrosus of the disc approached from a posterior aspect so that the nucleus pulposus can be treated with the therapeutic agent. Unfortunately, often approaching the annulus fibrosus from a posterior aspect can adversely affect the disc by causing further degeneration by tearing of the annulus fibrosus, as well as increasing the likelihood of herniation at the site of needle penetration.

Therefore, it would be beneficial to provide methods and devices that effectively treat a degenerative disc while reducing or preventing further damage from occurring to the disc, for example, reducing or preventing tearing of the annular fibrosus of the disc during treatment. It would be advantageous if the methods and devices approached the disc from alternative aspects, in addition to a posterior aspect.

SUMMARY

Methods and devices are provided to treat a degenerative disc while also reducing or preventing further damage from occurring to the disc, for example tearing of the annulus fibrosus, during treatment. In some embodiments, the methods and devices provided do not approach the disc from a posterior aspect. In some embodiments, a method of delivering a therapeutic agent to a nucleus pulposus of an intervertebral disc is provided. The method comprises inserting a delivery tool containing the therapeutic agent through an anterior portion, a lateral portion, or an anterolateral portion of an annulus fibrosus and into the nucleus pulposus of the intervertebral disc; and delivering the therapeutic agent to the nucleus pulposus of the intervertebral disc.

In some embodiments, a device for delivering a therapeutic agent to a nucleus pulposus of an intervertebral disc is provided. The device comprises a cannula configured to slidably receive the therapeutic agent and a needle. The cannula has a distal end that is configured to penetrate through an anterior portion, a lateral portion, posterior portion or an anterolateral portion of an annulus fibrosus and into the nucleus pulposus of the intervertebral disc. The needle is configured to slide in at least a portion of the cannula. The needle has a tip configured to contact the nucleus pulposus of the intervertebral disc and to deliver the therapeutic agent from the cannula to the nucleus pulposus of the intervertebral disc.

In some embodiments, a method of administering a therapeutic agent to an intervertebral disc is provided. The method comprises inserting a catheter into a blood vessel that leads to the nucleus pulposus of the intervertebral disc; and delivering the therapeutic agent through the catheter at or near the nucleus pulposus of the intervertebral disc.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures.

Figure 1:
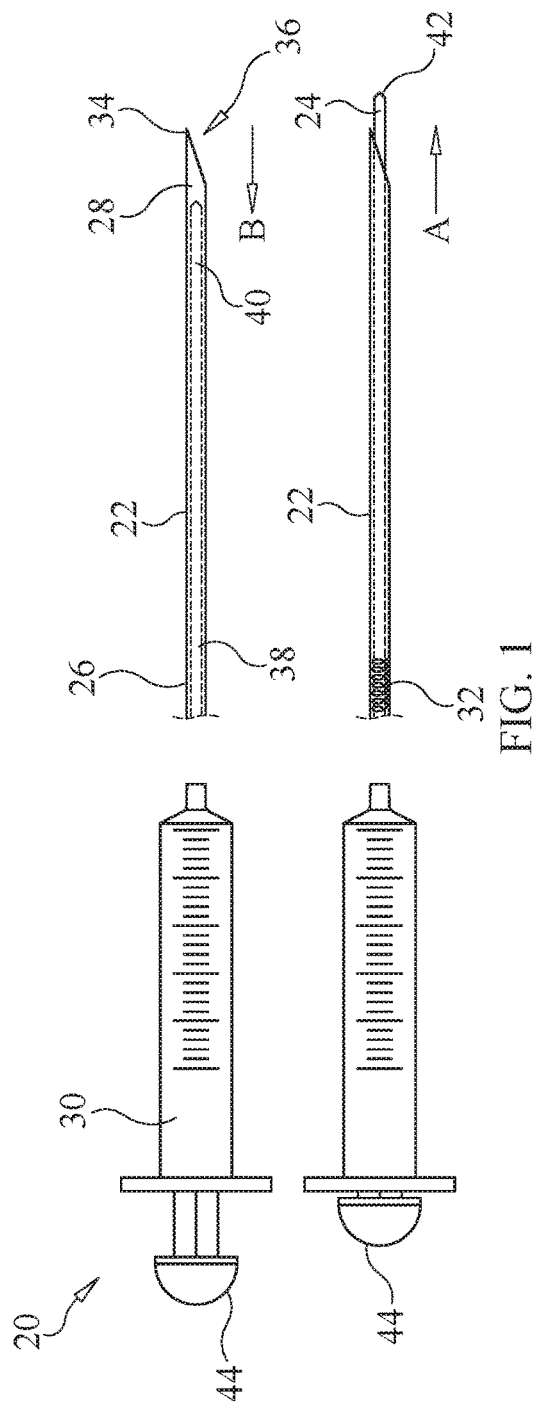
FIG. 1 is a perspective view of a device for delivering a therapeutic agent to a nucleus pulposus of an intervertebral disc. The device comprises a cannula configured to slidably receive the therapeutic agent and a needle.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "drug depot" includes but is not limited to capsules, microspheres, microparticles, microcapsules, microfibers particles, nanospheres, nanoparticles, coating, matrices, wafers, pills, pellets, emulsions, liposomes, micelles, gels, fiber, strip, sheet or other pharmaceutical delivery compositions or a combination thereof. The drug depot may comprise a depot that holds and administers the therapeutic agent. In some embodiments, the drug depot has pores that allow release of the therapeutic agent from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for therapeutic agent delivery. In some embodiments, the pores in the drug depot will be less than 250 to 500 microns. This pore size will prevent cells from infiltrating the drug depot and laying down scaffolding cells. Thus, in this embodiment, therapeutic agent will elute from the drug depot as fluid enters the drug depot, but cells will be prevented from entering. In some embodiments, where there are little or no pores, the therapeutic agent will elute out from the drug depot by the action of enzymes, by hydrolytic action and/or by other similar mechanisms in the human body.

The term "biodegradable" includes that all or parts of the drug depot will degrade over time by the action of enzymes, by hydrolytic action and/or by other similar mechanisms in the human body. In various embodiments, "biodegradable" includes that the depot can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In some embodiments, the drug depot can have pores that allow release of the therapeutic agent from the depot. The drug depot will allow fluid in the depot to displace the therapeutic agent. However, cell infiltration into the depot will be prevented by the size of the pores of the depot. In some embodiments, the pores in the drug depot will be less than 250 to 500 microns. This pore size will prevent cells from infiltrating the drug depot and laying down scaffolding cells. Thus, in this embodiment, the therapeutic agent will elute from the drug depot as fluid enters the drug depot, but cells will be prevented from entering. In some embodiments, where there are little or no pores, the therapeutic agent will elute out from the drug depot by the action of enzymes, by hydrolytic action and/or by other similar mechanisms in the human body.

The term "therapeutic agent" may be used interchangeably herein with the terms "drug", "therapeutically effective amount", and "active pharmaceutical ingredient". It will be understood that a "therapeutic agent" may include more than one therapeutic agent, wherein exemplary combinations of therapeutic agents include a combination of two or more drugs. The drug depot provides a concentration gradient of the therapeutic agent for delivery to the site. In various embodiments, the drug depot provides an optimal drug concentration gradient of the therapeutic agent at a distance of up to about 0.01 cm to about 20 cm from the administration site. In some embodiments, the drug depot provides continuous diffusion out the drug depot along a diffusion gradient until the therapeutic agent is all or substantially all released. This phenomenon is similar to a biologic "wicking" caused by the body tissues of the patient, which will always be at a lower diffusion gradient since the tissues will constantly be absorbing the therapeutic agent thus being at the lower end of the diffusion gradient as the tissue absorbs the therapeutic agent.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the decorticating devices described herein may obviously be disposed in different orientations when in use.

The phrases "sustained release," "sustain release" or "slow release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, gels, slabs, sheets, pellets, microparticles, microspheres, microcapsules, spheroids, shaped derivatives or paste. The formulations may be in a form that is suitable for suspension in isotonic saline, physiological buffer or other solution acceptable for injection into a patient. Further, the formulations may be used in conjunction with any implantable, insertable or injectable system that a person of ordinary skill would appreciate as useful in connection with embodiments herein including but not limited to parenteral formulations, microspheres, microcapsules, gels, pastes, implantable rods, pellets, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 hour.

Treating or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient.

As used herein, the terms "having," "containing," "including," "comprising," and the like are open ended terms that indicate the presence of stated elements or features, but do not preclude additional elements or features.

The term "discogenic back pain" refers to a disorder where one or more intervertebral discs are the source of pain. Discogenic back pain can include bulging, herniated, or ruptured discs which can trigger a response from proximate nerves, causing a pain sensation.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation; the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

Devices

A device 20, as shown in FIGS. 1-5B, is provided for delivering a therapeutic agent to a nucleus pulposus NP of an intervertebral disc ID (FIG. 6) while limiting damage or to prevent further damaging posterior aspects of an annulus fibrosus AF. The device comprises a cannula 22 configured to slidably receive the therapeutic agent and a needle 24. The cannula includes a proximal end 26 and a distal end 28. In some embodiments, the proximal end is configured to engage with a syringe 30 and a resilient member, such as spring 32 so that the needle can extend from the cannula.

The distal end of the cannula is configured to penetrate through an anterior portion, a lateral portion or an anterolateral portion of the annulus fibrosus and into the nucleus pulposus of the intervertebral disc. In some embodiments, the distal end includes a sharp beveled tip 34 that is sharper relative to a tip of the needle. The sharp beveled tip is configured to minimize procedure related pain and maximizes the ease of advancement and positioning in extra-discal soft tissue. The sharp beveled tip can be angled from about 5 degrees to about 60 degrees. In some embodiments, the sharp beveled tip can be angled from about 5, 10, 15, 20, 25, 30, 35, 40, 45, 50, 55 or 60 degrees. In some embodiments, the sharp tip can be variously shaped and can include a triangular, conical, tapered, trocar or square shape. In some embodiments, the tip is not sharp or beveled.

The needle is configured to slide in at least a portion of the cannula, such as a channel 36 of the cannula. The needle includes a proximal end 38 and a distal end 40. A tip 42 is defined at the distal end and is configured to contact the nucleus pulposus of the intervertebral disc and to deliver the therapeutic agent from the cannula to the nucleus pulposus of the intervertebral disc. In some embodiments, as shown in FIG. 1A, the tip of the needle is sharp. In some embodiments, the tip can have a length from about 1 to about 40 mm. In some embodiments, the length can be about 5 mm or can be about 30 mm. In some embodiments, the tip can have a length from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 to about 40 mm. In some embodiments, the needle is more flexible than the cannula so as to provide tactile feedback to a user. The tactile feedback and a high resistance created by the needle tip facilitates shallow intra-annular delivery of the therapeutic material.

Figure 1A:
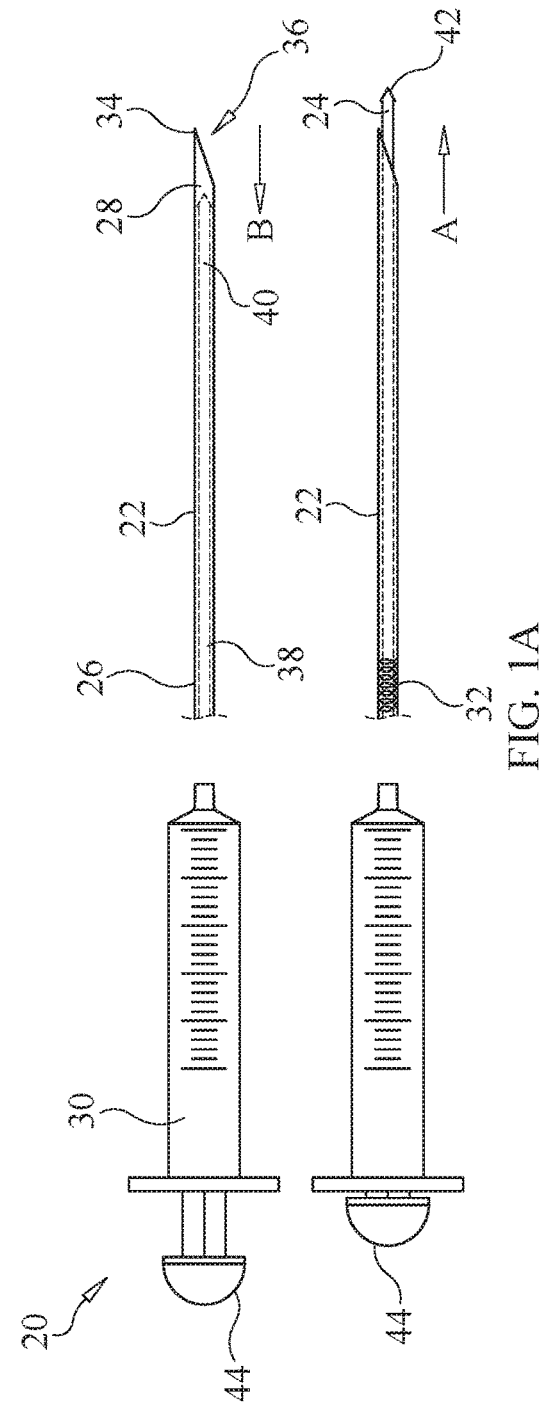
FIG. 1A is a perspective view of an embodiment of the device of FIG. 1 where a tip of the needle is sharp.

In some embodiments, the needle is slidable in a retracted position where the tip of the needle is within the cannula, and the needle is slidable in an extended position where the tip of the needle protrudes from the distal end of the cannula, as shown in FIG. 1. For example, a button 44 on the syringe can be pressed by a user so that the needle advances through the channel of the cannula and slides into the extended position, as shown by arrow A in FIG. 1. In some embodiments, the tip of the needle can protrude from the distal end of the cannula from about 5 to about 15 mm. In some embodiments, the tip can protrude from the distal end of the cannula from about 5, 6, 7, 8, 9, 10, 11, 12, 13, 14 to about 15 mm. The needle can then be retracted into the channel of the cannula when the button is pressed again, as shown by arrow B in FIG. 1.

Figure 2:
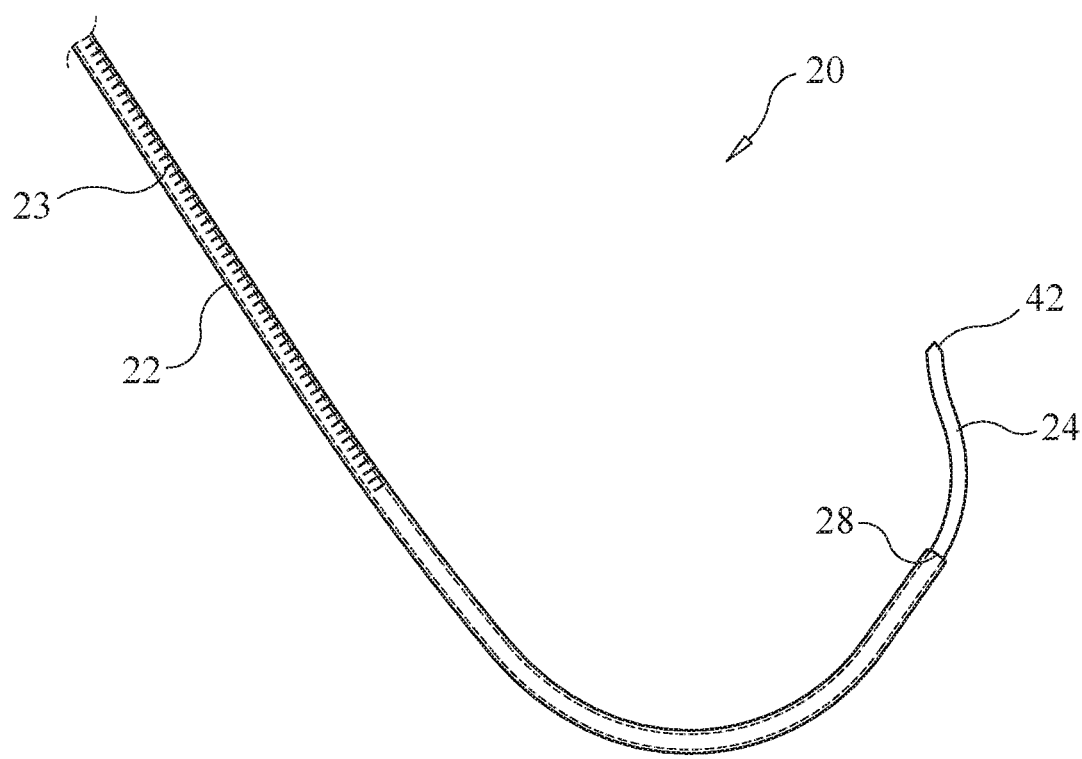
FIG. 2 is a perspective view of the device of FIG. 1 where the cannula and/or the needle is curved or hooked.

In some embodiments, as shown in FIG. 2, the cannula and/or the needle can be curved or hooked. In some embodiments, only the distal end of the cannula and/or the needle is curved or hooked. In some embodiments, the cannula and/or the needle is curved or hooked such that the needle and/or the cannula is capable of entering and curving downward into the nucleus pulposus during a procedure, as described herein. Thus, the instrument can approach the spine in the posterior position and the curve allows the cannula and/or needle to be positioned at an anterior portion, a lateral portion, or an anterolateral portion of an annulus fibrosus so that it can be penetrated to administer treatment to the nucleus pulposus of the intervertebral disc. For example, an entry point is created, and the therapeutic agent is delivered approaching from the posterior aspect of the spine, with a device, such as the device of FIG. 2, which enters and curves to the anterior of the annulus fibrosus/nucleus pulposus.

In some embodiments, all or a portion of the cannula can include visual indicia 23 which is configured to display how far the cannula has moved into the intervertebral disc, such as the nucleus pulposus. In some embodiments, the visual indicia can be displayed on a CT scan during the procedure. In some embodiments, the visual indicia are radiographic indicia, such as barium sulfate, calcium phosphate, and/or metal beads.

Figure 5:
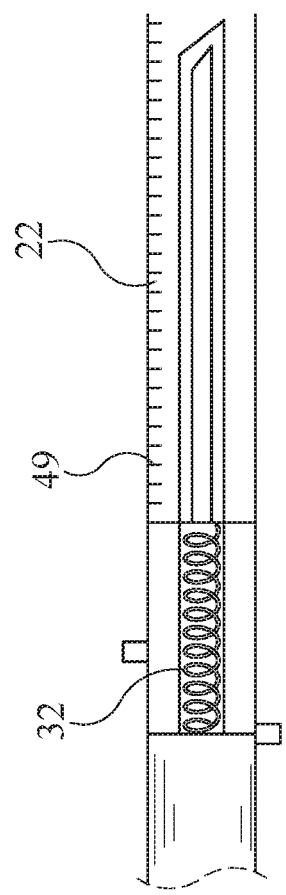
FIGS. 5, 5A and 5B are side views of a device used for administering a therapeutic agent to an intervertebral disc. The device comprises a cannula configured to slidably receive the therapeutic agent and a needle. A probe is disposed about at least a portion of the needle having an end configured to separate a portion of the annulus fibrosus from an endplate of the intervertebral disc.
Figure 5A:
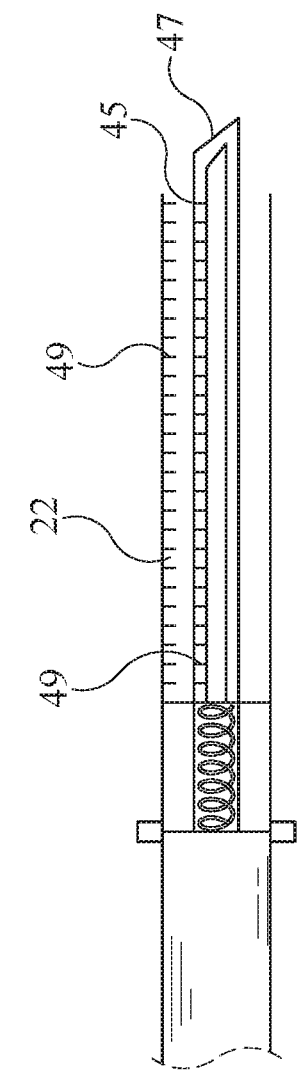
Figure 5B:
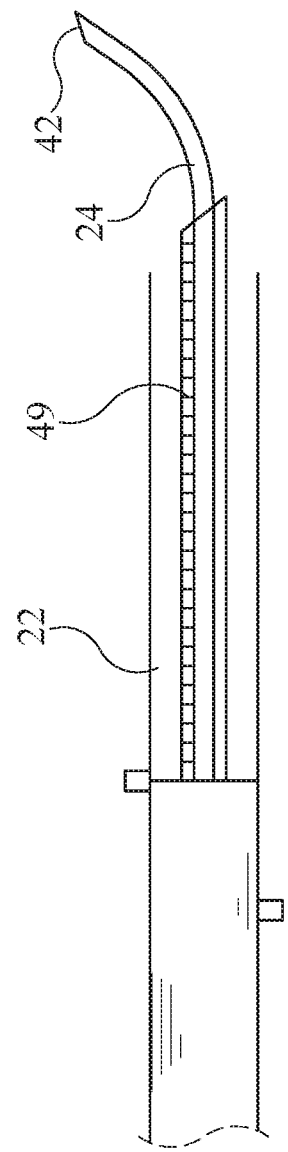
Figure 6:
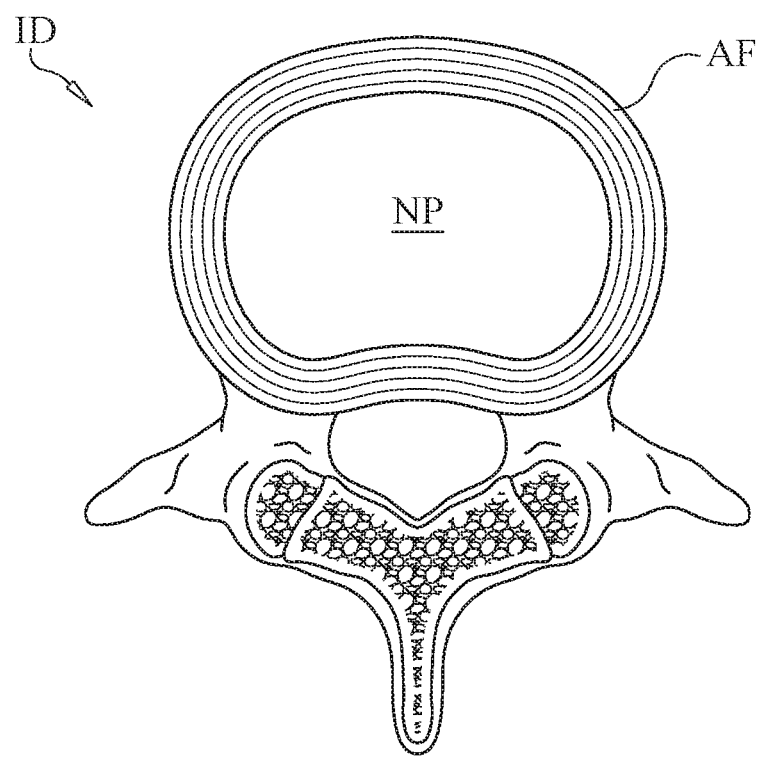
FIG. 6 is a cross-sectional side view an intervertebral disc of a patient. The intervertebral disc comprises a nucleus pulposus and an annulus fibrosus.

In some embodiments, as shown in FIGS. 5-5B, the device can alternatively comprise a probe 45. The probe is disposed about at least a portion of the needle having an end 47, as shown in FIG. 5A, and is configured to separate a portion of the annulus fibrosus from an endplate of the intervertebral disc. In some embodiments, the end of the probe is sharp or blunt. In this embodiment, the needle is curved, as shown in FIG. 5B, and can be made from a memory metal. The curved needle is configured to reduce or prevent damage from occurring to the annulus fibrosus and allows injection of the therapeutic agent into the interior of the intervertebral disc. Further, in this embodiment, the distal end of the cannula is blunt, as shown in FIG. 5 to facilitate tactile feedback, proper placement of the device and to prevent the cannula from penetrating the annulus fibrosus. In some embodiments, the cannula and/or the probe can include visual indicia 49, similar to visual indicia 23 shown in FIG. 2. The visual indicia is configured to indicate to a user the depth that the device has been inserted into the annulus fibrosus and/or whether the device has been rotated. In some embodiments, the visual indicia are radial. In some embodiments, the cannula has a larger diameter than the probe and the needle, and the probe has a larger diameter than the needle. In some embodiments, the cannula, the probe and/or the needle can have a diameter of from about 2 to about 6 mm. In some embodiments, the diameter can be from about 3 to about 4 mm. In some embodiments, the cannula, the probe and the needle are in coaxial alignment.

Figure 3:
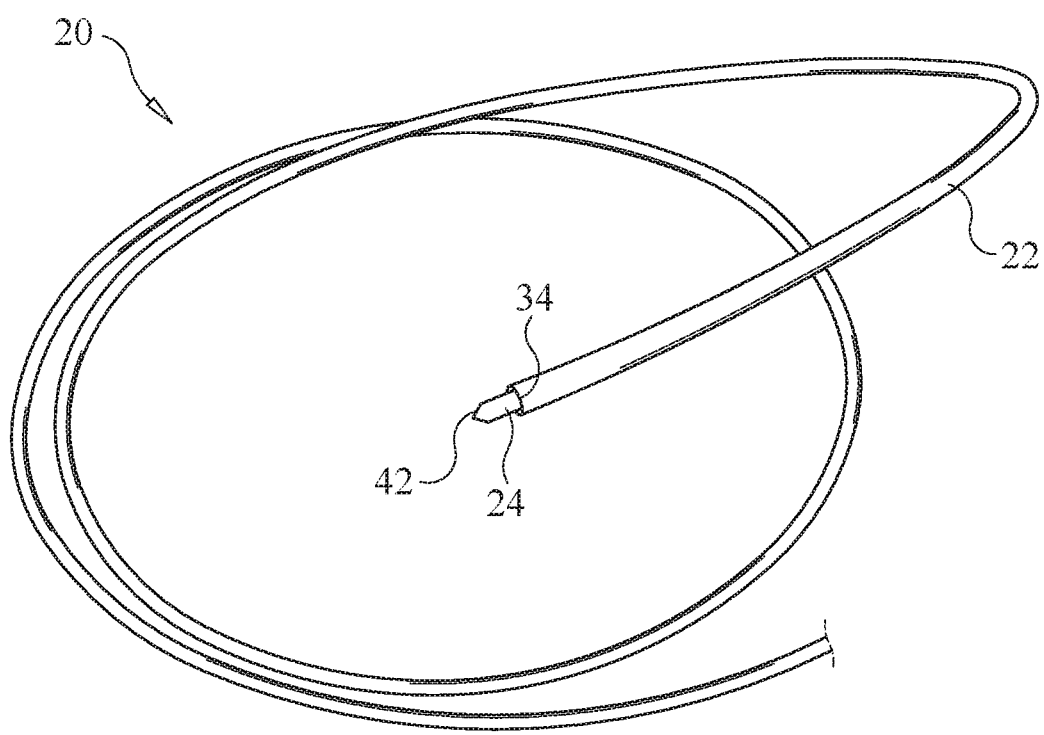
FIG. 3 is a perspective view of the device of FIG. 1 where the needle is coaxial to the cannula and the needle comprises a shape memory material.

In some embodiments, as shown in FIG. 3, the needle is coaxial to the cannula and the needle comprises a shape memory material. In some embodiments, the needle can be shaped so that it curves while being advanced into the nucleus pulposus during a procedure, as described herein. In some embodiments, the shape memory material comprises nitinol.

In some embodiments, the shape memory material can include polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Shape memory alloys include, but are not limited to TiNi, CuZnAl, and FeNiAl alloys. In some embodiments, the shape memory needle can be fabricated by injection molding of plastic materials comprising rigid, surgical grade plastic and/or metal materials.

In some embodiments, the needle has a gauge from about 4 to about 34 gauge. In some embodiments, the needle gauge can be from about 4, 6, 8, 10, 12, 14, 16, 18, 20, 22, 24, 26, 28, 30, 32 to about 34 gauge. In some embodiments, the cannula and/or the needle can be from about 16 to 200 mm in length.

In some embodiments, a lubricant is provided to assist in the insertion of the tip of the cannula into portions of the annulus fibrosus. In some embodiments, the lubricant can be, without limitation, polyethylene glycol (PEG), Glycerol, hyaluronic acid, hyaluronan, lubricin, polyethylene glycol, and any combinations thereof.

Figure 4:
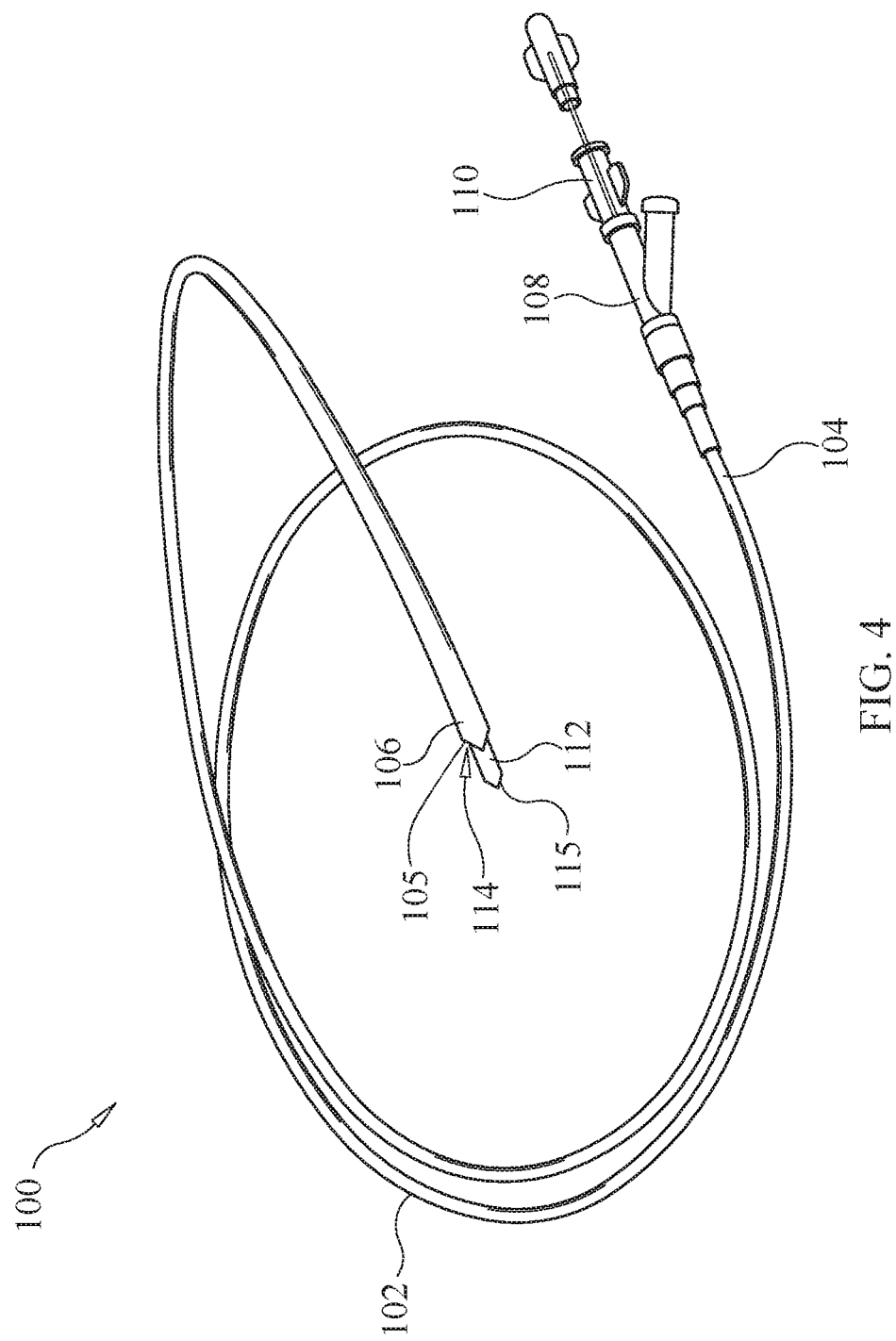
FIG. 4 is a perspective view of a catheter device used for administering a therapeutic agent to an intervertebral disc.

A device, such as a catheter 100, as shown in FIG. 4, is provided for administering a therapeutic agent to an intervertebral disc. In some embodiments, the catheter is configured to be inserted into a blood vessel that leads to the nucleus pulposus of the intervertebral disc and for delivering the therapeutic agent at or near the nucleus pulposus of the intervertebral disc, as described herein. The catheter can be used alone or in conjunction with the device of FIGS. 1-3. The catheter includes an elongated tubular body 102 that extends from a proximal end 104 to a distal end 106. The proximal end of the catheter is configured to engage with a luer fitting 108 and a syringe 110. The distal end can include a sharp point 105 configured to penetrate through blood vessels, cartilage and/or bone. The distal end of the catheter can be curved or straight and is configured to engage with the intervertebral disc and to administer the therapeutic agent.

In some embodiments, the catheter can be configured in a similar manner to cardiac catheters. In some embodiments, the catheter can be a certain size to accommodate the size of blood vessels. A guidewire 112 can be disposed for slidable engagement with a channel 114 of the catheter. In some embodiments, the guidewire can include a sharp pointed end 115 configured to penetrate through blood vessels, cartilage and/or bone.

Figure 7:
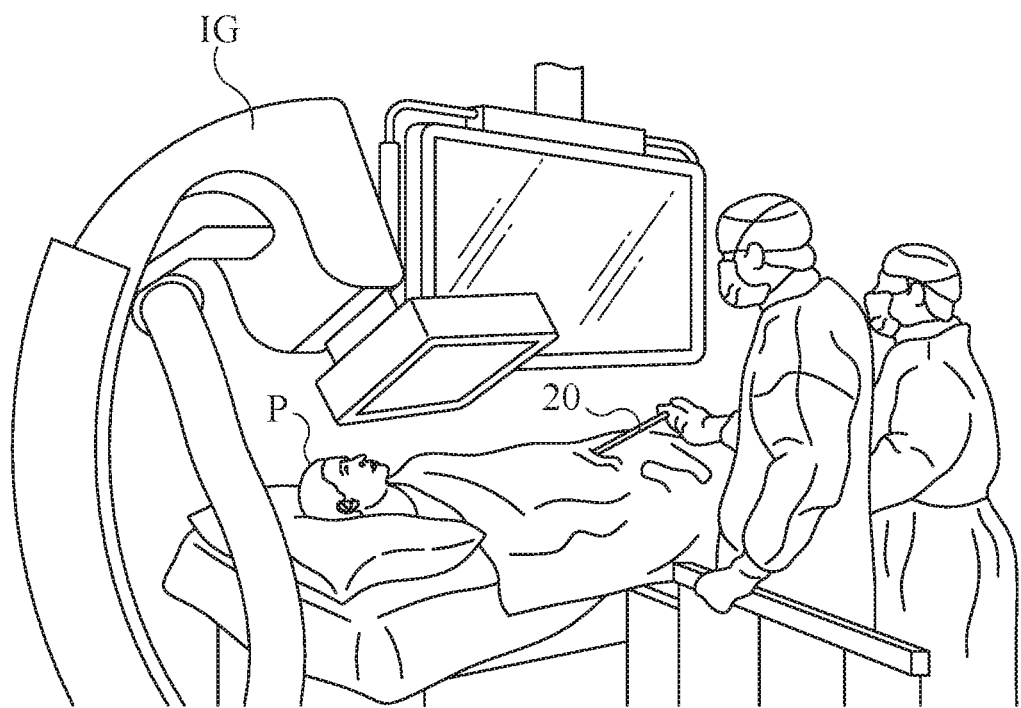
FIG. 7 is a perspective view of a patient in a supine position on a table in a procedure room. The patient is shown undergoing a procedure to treat a nucleus pulposus of an intervertebral disc with a therapeutic agent delivered by one of the devices of FIGS. 1-5B. Medical image guidance is used by a medical practitioner to assist the practitioner in the procedure.

In various aspects, the devices can also be coupled with an imaging guidance (IG) device, as shown in FIG. 7, such as ultrasound, CT, fluoroscopy or MRI, overhead 3D stereotactic system (via pre-procedure MRI and/or CT) allowing the user to visualize or otherwise identify the intervertebral disc. As shown in FIG. 7, a patient P can be placed in a supine position on a table in a procedure room and the devices described above, alone or in conjunction with image guidance and/or radiopaque materials can be used to treat a nucleus pulposus of an intervertebral disc with a therapeutic agent.

Figure 8:
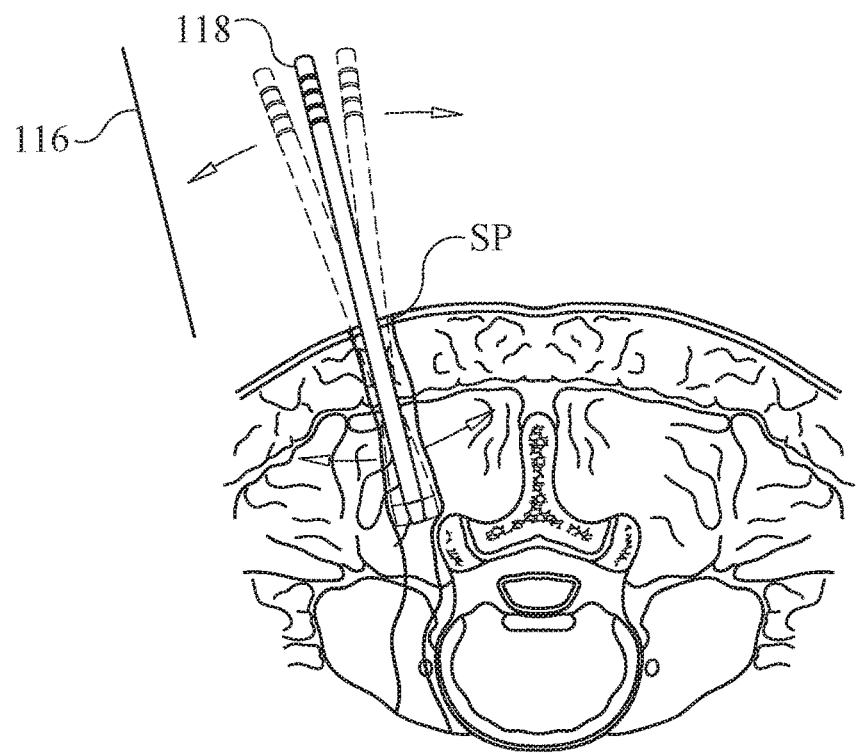
FIGS. 8, 9, 10 and 11 are perspective views of a guidewire, a plurality of dilators, a retractor, and/or a light source that are used during the procedure of FIG. 7.
Figure 9:
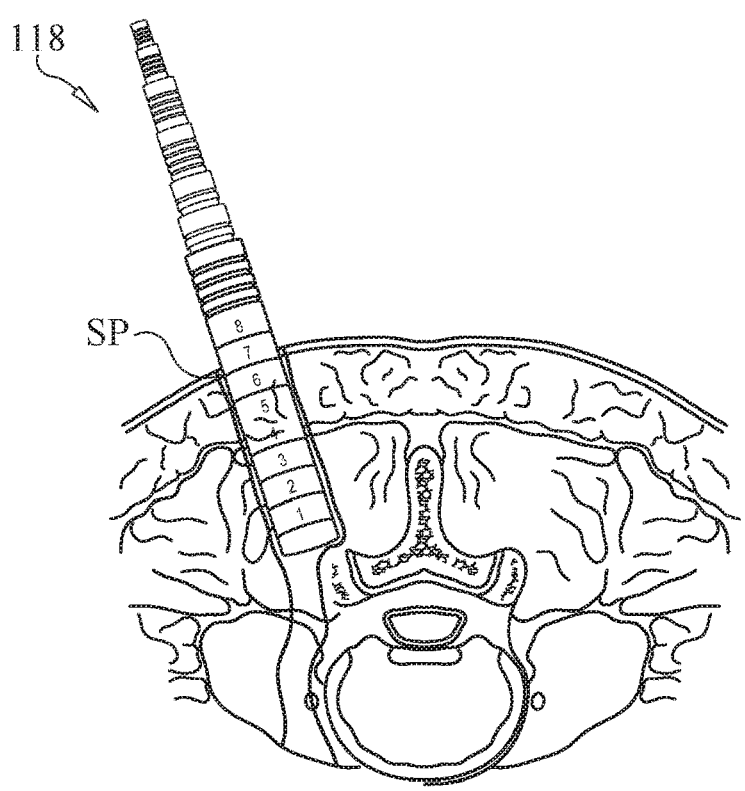
Figure 10:
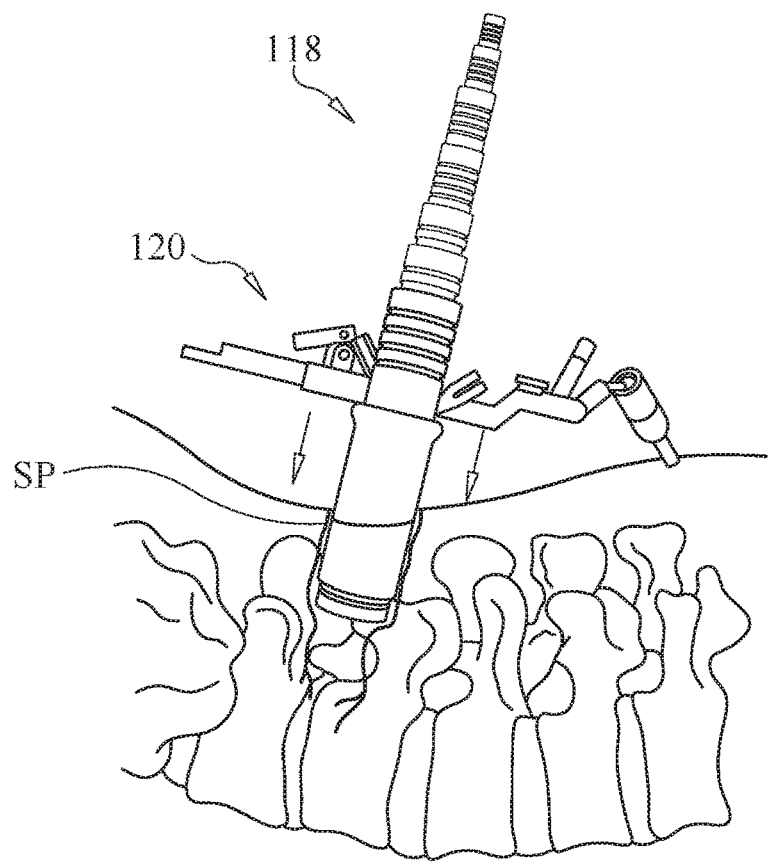
Figure 11:
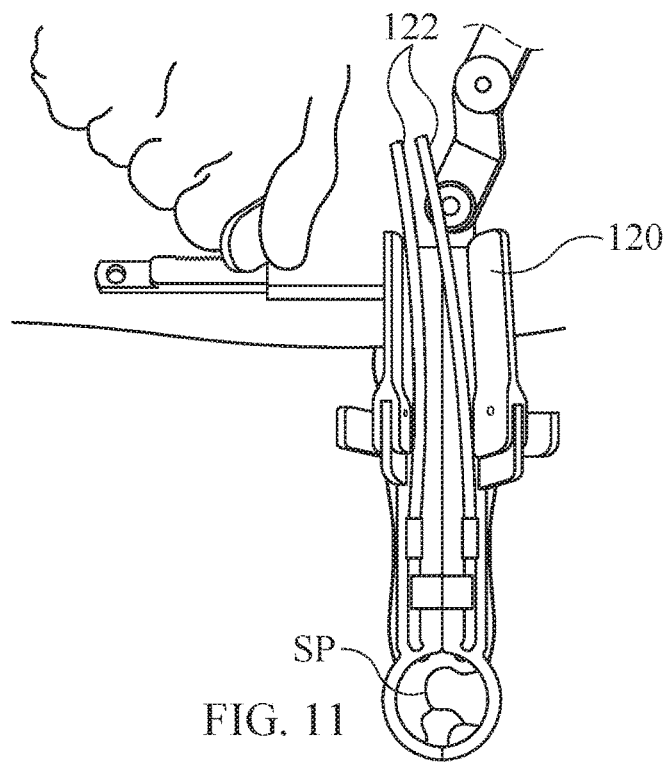

In some embodiments, as shown in FIGS. 8-11, before the device is implemented, various surgical tools can be used to access the intervertebral disc. For example, after an incision has been made in the patient, a guidewire 116 as shown in FIG. 8, similar to guidewire 112, can be inserted through the incision site to assist in creating a surgical pathway (SP). One or more dilators 118 can be used to palpate surrounding tissue and bone, as well as to identify proper dilator positioning, as shown in FIG. 8. As shown in FIG. 9, the one or more dilators can also be used to expand/enlarge the SP by dilating surrounding muscle and/or additional tissue. For example, the dilators can be sequentially placed over each other in order to expand/enlarge the SP. As shown in FIG. 10, a retractor 120 can be inserted over the one or more dilators and is locked in place. The dilators can then be removed, establishing the SP to the surgical site, as shown in FIG. 11. In some embodiments, a light source 122 can be provided to visually assist the surgeon during the procedure. In some embodiments, the procedure can include, but is not limited to a transforaminal lumbar interbody fusion (TLIF) procedure or an oblique lumbar interbody fusion (OLIF) procedure. It is to be understood that the dilators described above can be the same or different sizes than dilators for a TLIF interbody cage. In some embodiments, the devices, surgical tools and/or methods described herein can be used to treat a diseased vertebra or vertebrae and/or to prophylactically treat a non-diseased vertebra or vertebrae.

In some embodiments, components of the devices may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula, needle and/or catheter can include a funnel portion, plunger or tubular member may optionally include one or more tapered regions. In various embodiments, these components may be blunt, beveled, diamond point, ball tip, trocar tip, etc. These components may also have a tip style vital for accurate treatment of the patient depending on the surgical site. Examples of tip styles include, for example, Trephine, Cournand, Veress, Huber, Seldinger, Chiba, Francine, Bias, Crawford, deflected tips, Hustead, Lancet, or Tuohey. In some embodiments, the devices can be made from materials that are reusable, or alternatively made from materials that allow for a single, disposable use.

Methods

Figure 12:
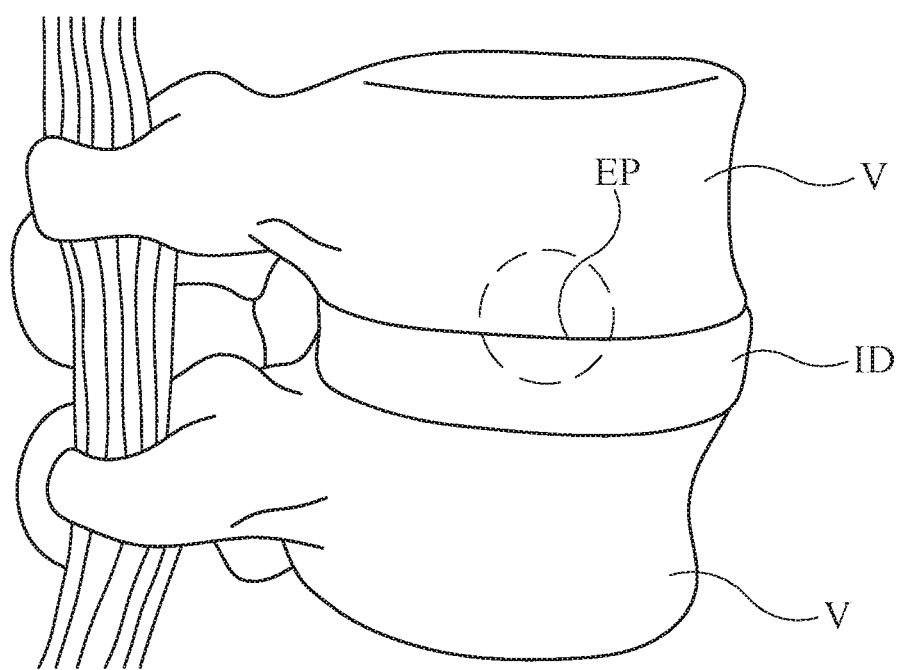
FIG. 12 is a perspective view of a section of a spine and a method of delivering a therapeutic agent to a nucleus pulposus of an intervertebral disc. An entry point is created at an endplate/annulus fibrosus interface and the therapeutic agent is delivered from the anterior or lateral aspect of the spine, with a device, such as the device of FIG. 2, which enters and curves downward to the nucleus pulposus.
Figure 13:
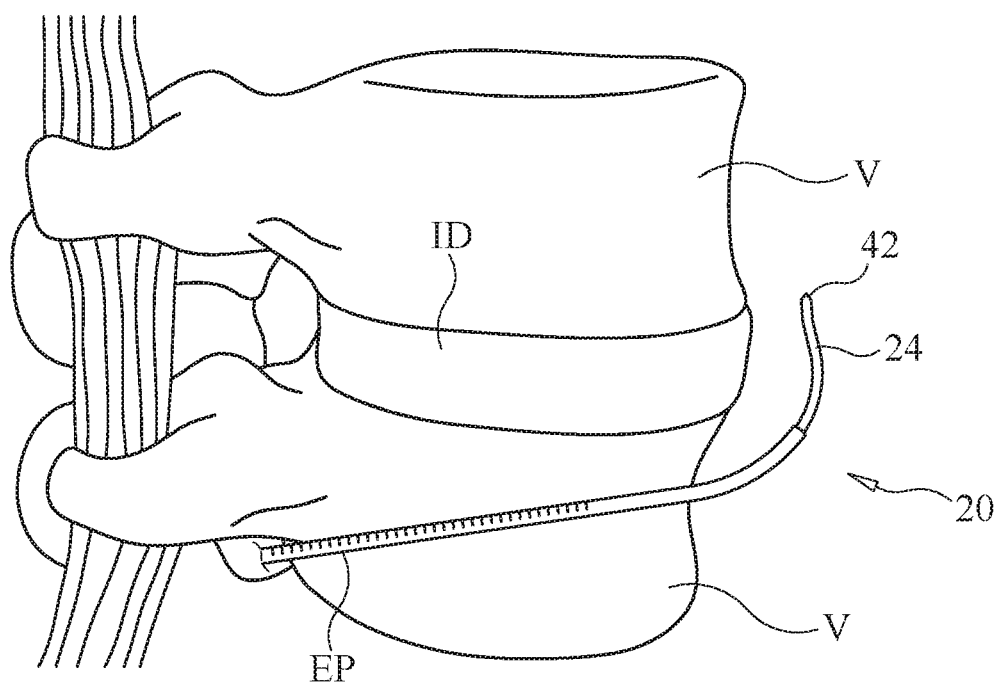
FIG. 13 is a perspective view of a section of a spine and a method of delivering a therapeutic agent to the annulus fibrosus/nucleus pulposus of an intervertebral disc. An entry point is created, and the therapeutic agent is delivered approaching from the posterior aspect of the spine, with a device, such as the device of FIG. 2, which enters and curves to the anterior of the annulus fibrosus/nucleus pulposus.
Figure 14:
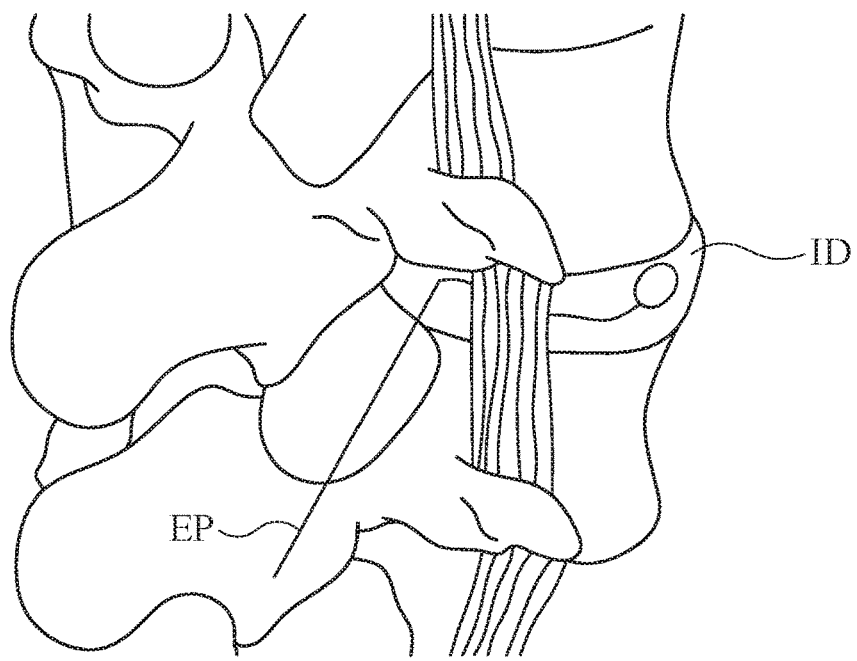
FIG. 14 is a perspective view of a section of a spine and a method of delivering a therapeutic agent to a nucleus pulposus of an intervertebral disc. A posterior entry point is created at the endplate/annular boundary and a device, such as the catheter of FIG. 4, follows the annulus fibrosus to a lateral or anterolateral position before penetrating the nucleus pulposus to deliver the therapeutic agent.

As shown in FIGS. 12-14, a method of delivering a therapeutic agent to a nucleus pulposus of an intervertebral disc is provided. The method comprises inserting a delivery tool containing the therapeutic agent through an anterior portion, a lateral portion, or an anterolateral portion of an annulus fibrosus and into the nucleus pulposus of the intervertebral disc; and delivering the therapeutic agent to the nucleus pulposus of the intervertebral disc. In some embodiments, the method is configured to insert the delivery tool into a portion of the annulus fibrosus other than from a posterior portion of the annulus fibrosus to reduce or prevent further damage from occurring to the annulus fibrosus during treatment. For example, further damage to the annulus fibrosus can include annular tearing. In some embodiments, by selecting to insert the delivery tool away from the posterior lateral annulus fibrosus, risk of future damage and herniation to the intervertebral disc is reduced.

In some embodiments, as shown in FIG. 12, an entry point (EP) of delivery is created with a surgical tool at an endplate/annulus fibrosus interface before the delivery tool is inserted. The EP is created from an anterior or lateral aspect of the spine. In some embodiments, the surgical tool can be a drill or other tool that is thin enough to operate in a confined space. The EP is used as an access point for the delivery tool. The delivery tool is then inserted through the anterior portion or the lateral portion. In some embodiments, the delivery tool is device 20 of FIG. 2. The delivery tool will then enter into the EP and curve downward or in a direction to access the nucleus pulposus. The therapeutic agent will then be inserted into the delivery tool and administered to the nucleus pulposus.

In some embodiments, as shown in FIG. 13, an EP of delivery is created with a surgical tool, as described above, posterior to the spine before the delivery tool is inserted. The delivery tool is then inserted through posteriorly. In some embodiments, the delivery tool is device 20 of FIG. 2. The delivery tool will then enter into the EP and curve downward or in a direction, to avoid the posterior annulus and to access the nucleus pulposus. The therapeutic agent will then be inserted into the delivery tool and administered to the nucleus pulposus. In this embodiment, the device avoids the posterior annulus fibrosus due in part to the device of FIG. 2 being curved or hooked.

In some embodiments, as shown in FIG. 14, a posterior EP of delivery is created with the surgical tool. The delivery tool is then introduced. In some embodiments, the delivery tool is device 20 of FIG. 3. The delivery tool is then inserted into the EP and the cannula is advanced from the posterior aspect and follows the annulus fibrosus curvature anteriorly. When in position in the anterior-lateral aspect, the needle is advanced in a curved aspect to enter the central nuclear space. The therapeutic agent will then be inserted into the delivery tool and administered to the nucleus pulposus. In this way, penetrating the posterior aspect of the spine is reduced and/or avoided so as to reduce damage to the posterior aspect of the annulus fibrosus of the disc.

In some embodiments, the methods depicted in FIGS. 12-14 can be performed using device 20 shown in FIG. 1. For example, the device is introduced with the needle being placed in the retracted position. The needle is then guided through soft tissue until it is positioned near the selected intervertebral disc, at a trajectory aligned with desired EP, described above. The needle is then deployed from the cannula and placed in an extended position, and extends up to approximately 5 mm from the beveled tip of the cannula. The therapeutic material is then delivered to the annulus fibrosus and/or the nucleus pulposus. In some embodiments, the feedback and resistance provided by the tactile tip facilitates shallow intra-annular delivery of the therapeutic material. In some embodiments, the beveled tip minimizes procedure-related pain and maximizes the ease of advancement and positioning in extra-discal soft tissue.

As shown in FIGS. 15-18, a method of administering a therapeutic agent to an intervertebral disc is provided. The method comprises inserting a catheter into a blood vessel that leads to the nucleus pulposus of the intervertebral disc; and delivering the therapeutic agent through the catheter at or near the nucleus pulposus of the intervertebral disc. In some embodiments, the catheter is catheter 100 of FIG. 4 and the therapeutic agent is delivered to the catheter by syringe 110. It is to be understood that the vascular system of the intervertebral disc is accessed using standard endovascular techniques.

Figure 15:
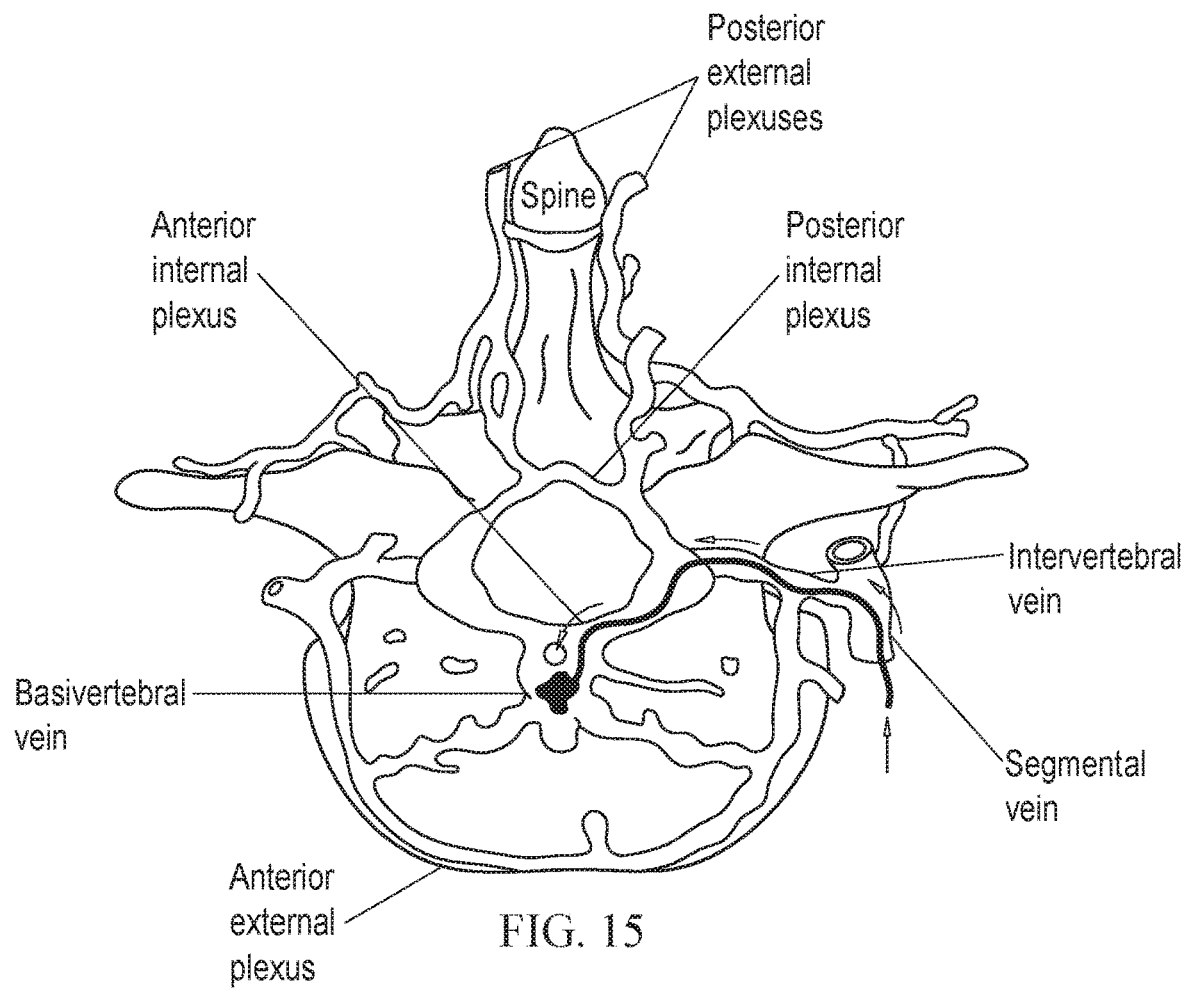
FIG. 15 is a transverse cross-sectional view of a thoracic vertebra and a method of administering a therapeutic agent to an intervertebral disc. Access to the nucleus pulposus is shown by an endovascular approach through the segmental vein and then to the basivertebral vein. A catheter, such as the catheter of FIG. 4 and/or a guidewire is guided into the basivertebral vein and through the endplate and to the nucleus pulposus to deliver the therapeutic agent.
Figure 16:
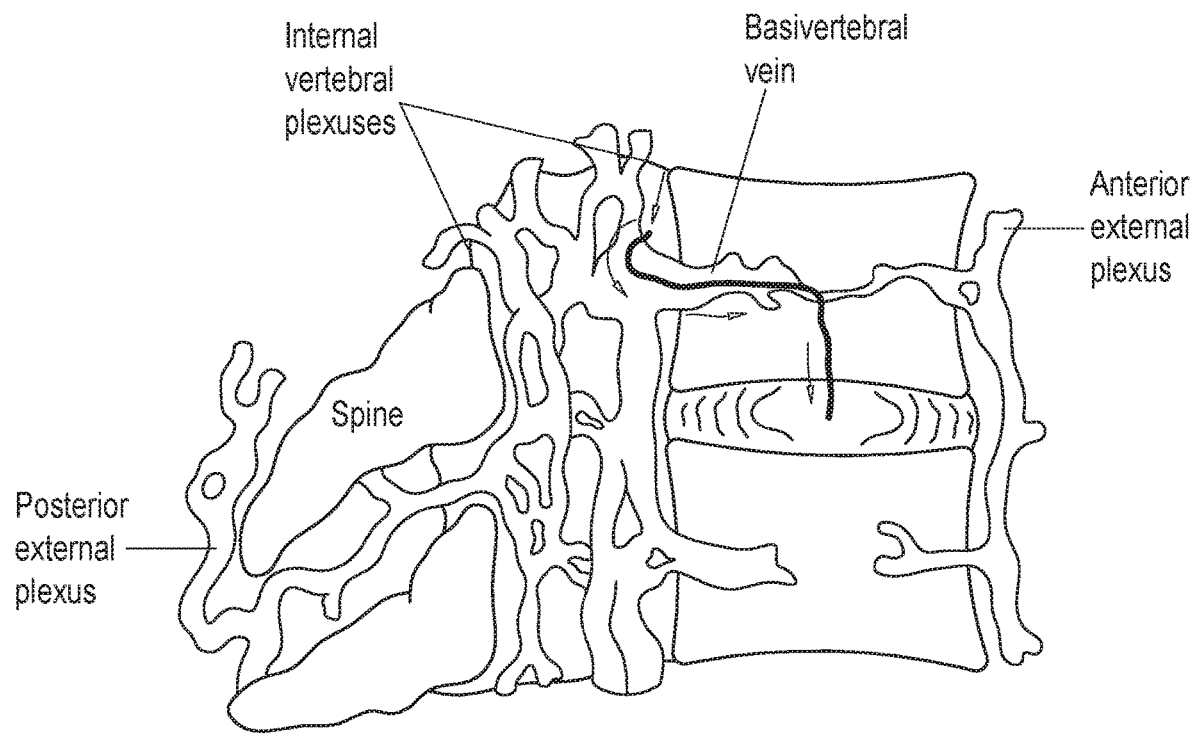
FIG. 16 is a median sagittal sectional view of the thoracic vertebra and the method described in FIG. 15.

In some embodiments, as shown in FIGS. 15 and 16, the blood vessel is the segmental vein that leads to the basivertebral vein in the center of the vertebral body, or the blood vessel is the segmental vein that leads to the basivertebral artery. The path of the catheter is then directed approximately axially to penetrate the basivertebral vein or artery, and through the cancellous bone of the vertebral body to penetrate an endplate to access the nucleus pulposus of the intervertebral disc. In some embodiments, the catheter and/or the guidewire are used for penetration. The therapeutic agent is then delivered to the nucleus pulposus by the catheter. In some embodiments, the path of the catheter is configured to translate in the same direction of blood flow. In some embodiments, the path of the catheter is configured to translate in the opposite direction of blood flow.

It will be understood by those of ordinary skill in the art that soft tissue (e.g., muscle, cartilage, skin tissue, organ tissue, etc.) as well as hard tissue (e.g., bone, teeth) can be penetrated by the delivery tool (e.g., cannula, needle, etc.) to access the blood vessel that branches at or near the annulus fibrosus and/or nucleus pulposus to deliver the treatment to the target site of the intervertebral disc.

Figure 17:
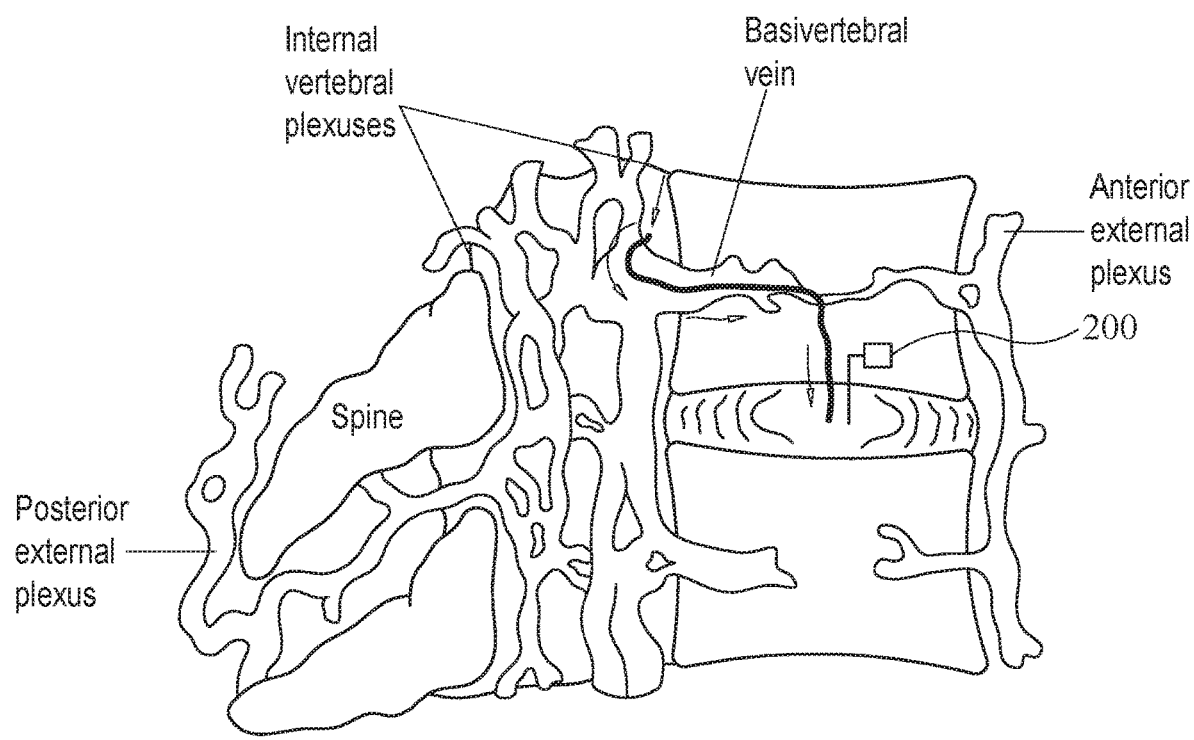
FIG. 17 is a median sagittal sectional view of the thoracic vertebra and a method of administering a therapeutic agent to an intervertebral disc. The intervertebral disc is accessed through vasculature, as described above by a catheter, such as the catheter of FIG. 4, and a drug depot containing the therapeutic agent is administered to the vertebral body for slow release into the nucleus pulposus over a period of time.

In some embodiments, as shown in FIG. 17, the intervertebral disc is accessed in the same matter as described in the method of FIGS. 15 and 16, however, in this embodiment, before the therapeutic agent is delivered to the nucleus pulposus, the catheter and/or the guidewire are retracted back into the vertebral body. A void V can be formed in a portion of the cancellous bone of the vertebral body and a portion of the endplate by penetrating those areas with the catheter. In some embodiments, the void has direct access to the nucleus pulposus. The therapeutic agent is then delivered into the void at the vertebral body by a drug depot 200. In some embodiments, the drug depot is configured for sustained release of the therapeutic agent to the nucleus pulposus over a period of time. In some embodiments, the drug depot is injected into the void for example, by a syringe or the catheter. In some embodiments, the drug depot is a hydrogel having a selected release profile.

It will be understood by those of ordinary skill in the art that direct access to the annulus fibrosus or the nucleus pulposus of the intervertebral disc includes inserting the device into, among other things, a blood vessel, such as an artery, vein, arteriole, venule, or capillary, or a blood vessel that may branch into another artery, vein, arteriole, venule, or capillary that directly leads to the annulus fibrosus or the nucleus pulposus of the intervertebral disc.

It will be understood by those of ordinary skill in the art that indirect access to the annulus fibrosus or the nucleus pulposus of the intervertebral disc includes inserting the device into a blood vessel, such as an artery, vein, arteriole, venule, or capillary or a blood vessel that may branch into an artery, vein, arteriole, venule, or capillary that indirectly leads to the annulus fibrosus or the nucleus pulposus of the intervertebral disc, where the treatment can be administered without penetrating the annulus fibrosus or the nucleus pulposus of the intervertebral disc.

Figure 18:
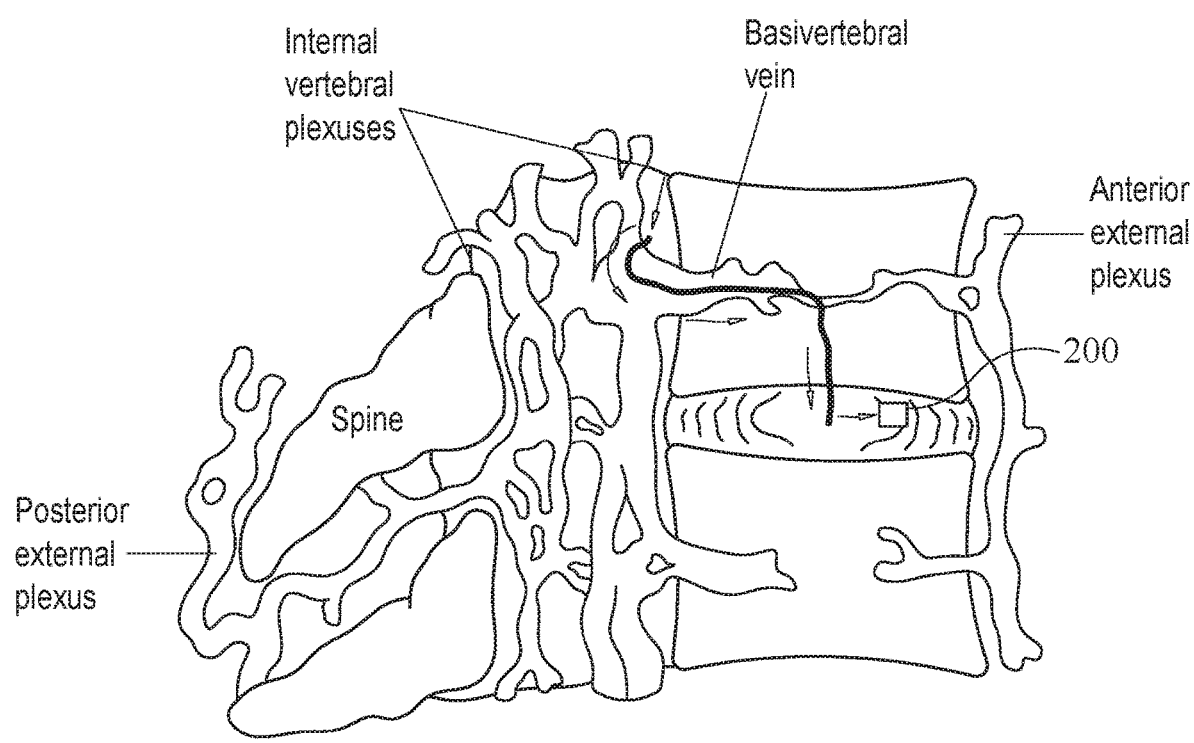
FIG. 18 is a median sagittal sectional view of the thoracic vertebra and a method of administering a therapeutic agent to an intervertebral disc. The intervertebral disc is accessed through the vasculature described above by a curved instrument, such as the device of FIG. 2, and a drug depot containing the therapeutic agent is administered to the annulus fibrosus for slow release into the nucleus pulposus over a period of time.

In some embodiments, as shown in FIG. 18, the intervertebral disc is accessed in the same matter as described in the method of FIGS. 15 and 16. However, in this embodiment, instead of penetrating the nucleus pulposus after endplate penetration, a curved device is used to access the void. In some embodiments, the device can be device 20 of FIG. 2. The device is inserted into the void, and the annulus fibrosus of the intervertebral disc and/or the nucleus pulposus is accessed by the curved instrument. In some embodiments, the therapeutic agent is then delivered to the annulus fibrosus by a drug depot for sustained release of the therapeutic agent to the nucleus pulposus over a period of time. In some embodiments, the drug depot is injected into the annulus fibrosus, for example, the device 20 of FIG. 2, by a syringe or the catheter.

In some embodiments, the intervertebral disc is approached via the vertebral body in the same matter as described in the method of FIGS. 15 and 16. However, in this embodiment, the catheter does not enter the intervertebral disc space. Instead, the therapeutic agent is released into the vertebral venous plexus in the superior vertebral body. To promote extravasation of the therapeutic agent, the therapeutic agent is administered in a drug depot containing one or more promoters of diapedesis. In some embodiments, the one or more promoters of diapedesis include, but is not limited to, an antagonist/antibody for the spingosine-1-phosphate receptor, recombinant ICAM-1, or an endothelial irritant that promotes localized inflammation, thereby increasing the permeability of the vascular lumen. In some embodiments, administration of one or more promoters of diapedesis allows cells or large molecules to traverse the otherwise tight junctions of the vascular lumen and diffuse from the endplate into the target disc space.

In some embodiments, the catheter can be used in conjunction with other devices to assist in the procedure. In some embodiments, the tools can include, but are not limited to balloons, stents, closure devices, and/or image guidance devices.

In various aspects, image guidance devices, as shown in FIG. 7, such as ultrasound, CT, fluoroscopy or MRI, overhead 3D stereotactic system (via pre-procedure MRI and/or CT) allow the user to visualize or otherwise identify the intervertebral disc. For example, imaging devices useful in coupling with the methods and devices described herein comprise, without limitation, Magnetic Resonance Imaging (MRI), functional Magnetic Resonance Imaging (fMRI), Magnetic Resonance Spectroscopy (MRS), diffusion MRI (DWI), diffusion tensor MRI (DTI), electroencephalography (EEG), magnetoencephalography (MEG), nuclear neuroimaging, positron emission tomography (PET), single photon emission computed tomography (SPECT), Ictal-Interictal SPECT Analysis by Statistical Parametric Mapping (ISAS), Computed Tomography (CT), x-ray, fluoroscopy, angiography, ultrasonography, transcranial magnetic stimulation (TMS), transcranial direct current stimulation (tDCS), transcranial electrical stimulation (TES), motor evoked potential (MEP), somatosensory evoked potential (SSEP), phase reversal of somatosensory evoked potential, evoked potential, electrocorticography (ECoG), direct cortical electrical stimulation (DCES), microelectrode recording (MER) or local field potential recording (LFP).

In some embodiments, various navigational and/or robotics systems, devices and software can be used to assist in administering the therapeutic agent to the patient. For example, Mazor X™ Stealth Edition, StealthStation™, Mazor X™, and/or O-Arm™ owned by Medtronic located in Minneapolis, Minn. can be used.

In various embodiments, one or more components of the devices are sterilized by radiation in a terminal sterilization step in the final packaging. Terminal sterilization of a product provides greater assurance of sterility than from processes such as an aseptic process, which requires individual product components to be sterilized separately and the final package assembled in a sterile environment.

In various embodiments, gamma radiation is used in the terminal sterilization step, which involves utilizing ionizing energy from gamma rays that penetrate deeply into the bone material dispensing device. Gamma rays are highly effective in killing microorganisms, they leave no residues, nor do they have sufficient energy to impart radioactivity to the apparatus. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the bone material dispensing device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the device including, but not limited to, gas sterilization such as, for example, with ethylene oxide or steam sterilization.

Therapeutic Agent

In some embodiments, the therapeutic agent comprises a depot, a gel, hydrogel, stem cells, discogenic cells, platelet rich plasma, blood, bone marrow concentrate, cytokines, growth and differentiation factors, buffers, saline, hyaluronic acid, micronized autologous intervertebral disc, micronized allogenic intervertebral disc, cartilage, or a combination thereof.

In some embodiments, the therapeutic agent can be mixed with a liquid material such as a suitable diluent and then loaded into the devices. The cannula may have enough space to allow for the therapeutic agent and a volume of diluent to be mixed. In some embodiments, the diluent includes dextrose, other sugars including but not limited to sucrose, fructose, glucose, lactated ringer's, polyols including, but not limited to, mannitol, xylitol, sorbitol, maltitol, lactitol, polysaccharides including, but not limited to, native or pre-gelatinized starch, maltodextrins, cyclodextrins, mineral compounds including, but not limited to, dicalcium or tricalcium phosphate, either dihydrate or anhydrous, cellulose derivatives including, but not limited to, microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline or 0.45% saline. In some embodiments, other delivery vehicles can be used for example, D5W (dextrose in 5% water), D5NS (dextrose in 5% water and normal saline) and D5W/1/2NS (D5W and ½ normal saline), blood, mesenchymal stem cells, or the like.

In some embodiments, the therapeutic agent can include, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents can include BMP-1 and/or BMP-2, as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2 or heterodimers thereof. Recombinant BMP-2 can be used at a concentration of about 0.4 mg/mL to about 10.0 mg/mL, preferably about 1.5 mg/mL.

The therapeutic agent may be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

In some embodiments, the therapeutic agent can include, but is not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The therapeutic agent may include excitatory amino acids such as glutamate and aspartate, antagonists or inhibitors of glutamate binding to NMDA receptors, AMPA receptors, and/or kainate receptors. The therapeutic agent may reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

In some embodiments, the therapeutic agent may include, but is not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The therapeutic agent may include, but is not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The therapeutic agent may include, but is not limited to, a statin. Examples of a useful statin include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Application Publication No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the therapeutic agent can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefornide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin;

dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin G benzathine, penicillin G potassium, penicillin G procaine, penicillin G sodium, penicillin V, penicillin V benzathine, penicillin V hydrabamine, and penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent can be an antiviral agent that can be mixed with the therapeutic agent. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Drug Depot

In some embodiments, the therapeutic agent is delivered at or near the annulus fibrosus or the nucleus pulposus of the intervertebral disc or a void located at or near the intervertebral disc by drug depot 200, as shown in FIGS. 17 and 18. In some embodiments, the drug depot includes, but is not limited to a hydrogel, capsules, microspheres, particles, coating, matrices, wafers, pills, pellets or other pharmaceutical delivery compositions.

In various embodiments, the depot may comprise a bioerodible, a bioabsorbable, and/or a biodegradable biopolymer that may provide immediate release, or sustained release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In various embodiments, the drug depot comprises drug pellets, loaded with a therapeutically effective amount of the therapeutic agent. In various embodiments, the drug pellets comprise a gel or hydrogel in viscous forms and microspheres loaded with a therapeutic agent. The pellet can be any shape, such as for example, bullet shaped, spherical, substantially spherical, flaked, rod shaped, square, oval, etc.

In some embodiments, a therapeutically effective amount of the therapeutic agent can be administered by the drug depot at or near the intervertebral disc. "Therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In some embodiments, the drug depot has a selected drug release profile and the therapeutic agent is delivered at or near the intervertebral disc over a period of time. In some embodiments, the drug depot is designed to immediately release the therapeutic agent. In other embodiments, the drug depot is designed for sustained release. In other embodiments, the drug depot comprises one or more immediate release surfaces and one or more sustained release surfaces. In some embodiments, the drug depot releases the therapeutic agent over a period from about 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 5 days, 10 days, 15 days, 20 days, 25 days, 30 days, 1 month, 2 months, 3 months, 4 months, 5 months, 6 months, 7 months, 8 months, 9 months, 10 months, 11 months to 1 year.

In various embodiments, the drug depot can be designed to cause an initial burst dose of therapeutic agent within the first 24 hours to 48 hours after implantation. "Initial burst" or "burst effect" "burst release" or "bolus dose" refers to the release of therapeutic agent from the drug depot during the first 24 hours to 48 hours after the drug depot comes in contact with an aqueous fluid. The "burst effect" is believed to be due to the increased release of therapeutic agent from the drug depot. In some embodiments, the drug depot has one or more burst release surfaces that releases about 10%, 15%, 20%, 25%, 30%, 35%, 45%, to about 50% of the drug over 24 or 48 hours.

In some embodiments, the drug depot has a modulus of elasticity in the range of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$. In some embodiments, the drug depot is in the form of a solid.

In some embodiments, the therapeutic agent is administered in a drug depot that is solid or in semi-solid form. The solid or semi-solid form of the drug depot may have a pre-dosed viscosity in the range of about 1 to about 2000 centipoise (cps), 1 to about 200 cps, or 1 to about 100 cps. After the solid or semi-solid drug depot is administered to the target site, the viscosity of the semi-solid or solid depot will increase and the semi-solid will have a modulus of elasticity in the range of about $1\times10^2$ to about $6\times10$ dynes/cm$^2$, or $2\times10^4$ to about $5\times10^5$ dynes/cm$^2$, or $5\times10^4$ to about $5\times10^5$ dynes/cm$^2$.

In various embodiments, the semi-solid or solid drug depot may comprise a polymer having a molecular weight (MW), as shown by the inherent viscosity (IV), from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

Degradation times for the polymers could be one day to 1 year. In some embodiments, the degradation time is about 1 day to about 180 days. In some embodiments, the degradation time is about 1 day, 5 days, 10 days, 15 days, 30 days, 60 days, 90 days, 120 days, 150 days, 180 days, 210 days, 240 days, 270 days, 300 days, 340 days to about 1 year.

Kit

In various embodiments, a kit can be provided containing the devices prefilled with the therapeutic agent or the kit can contain the devices. In some embodiments, the kit may include additional parts along with the devices such as the therapeutic agent, syringes, lubricant, tubing and dilators (e.g., wipes, needles, etc.). The kit may include one of the devices in a first compartment. The second compartment may include the therapeutic agent sealed in a container or within a syringe, along with a vial containing diluent and any other delivery instruments needed for the localized delivery. A third compartment may include gloves, drapes, wound dressings and other procedural supplies for maintaining sterility, as well as an instruction booklet, which may include a chart that shows how to administer the therapeutic agent. A fourth compartment may include additional needles, fasteners, tissue adhesive, and/or sutures. Each tool may be separately packaged in a plastic pouch that is radiation sterilized. A fifth compartment may include an agent for radiographic imaging. A cover of the kit may include illustrations of the procedure and a clear plastic cover may be placed over the compartments to maintain sterility.

It is to be understood that persons skilled in the art will recognize that two or more embodiments may be combined without departing from the spirit and scope of the disclosure.

Although the invention has been described with reference to embodiments, persons skilled in the art will recognize that changes may be made in form and detail without departing from the spirit and scope of the disclosure.

What is claimed is:

1. A method of delivering a therapeutic agent to a nucleus pulposus of an intervertebral disc, the method comprising:
   placing a needle in a retracted position in which a distal end of the needle entirely resides in a first channel of a probe that is disposed about at least a portion of the needle;
   placing the probe in a retracted position in which a distal end of the probe entirely resides in a second channel of a cannula, the cannula comprising a distal end with a beveled tip sharper than a tip of the needle and is disposed about at least a portion of the probe;
   inserting at least a portion of the delivery tool into a body towards an annulus fibrosus of the intervertebral disc, the delivery tool comprising the cannula, the probe and the needle;
   using the beveled tip of the cannula to penetrate through the annulus fibrosus while the needle and probe are in their retracted positions;
   causing the needle and probe to simultaneously slide within the second channel towards a free end of the cannula such that the probe and needle transitions from their respective retracted positions to respective extended positions in which at least a portion of the distal ends of the needle and probe protrude out from the cannula;
   using the probe to separate a portion of the annulus fibrosus from an endplate of the intervertebral disc;

advancing the distal end of the needle out of the first channel of the probe and into the nucleus pulposus of the intervertebral disc; and using the needle to facilitate delivery of the therapeutic agent from the delivery tool to the nucleus pulposus of the intervertebral disc.

2. The method of claim 1, wherein the method further comprises forming an entry point of delivery with a surgical tool between an endplate and an annular body before inserting the delivery tool, and inserting the delivery tool through an anterior portion or a lateral portion.

3. The method of claim 1, wherein the method further comprises forming a posterior entry point of delivery with a surgical tool, and inserting the delivery tool is done from a lateral or anterolateral portion of the annulus fibrosus.

4. The method of claim 2, wherein the surgical tool is a drill.

* * * * *